(12) United States Patent
Naito

(10) Patent No.: US 9,028,397 B2
(45) Date of Patent: May 12, 2015

(54) MEDICAL APPARATUS

(75) Inventor: Kimihiko Naito, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 247 days.

(21) Appl. No.: 13/237,151

(22) Filed: Sep. 20, 2011

(65) Prior Publication Data

US 2012/0065628 A1    Mar. 15, 2012

Related U.S. Application Data

(63) Continuation of application No. PCT/JP2011/061094, filed on May 13, 2011.

(30) Foreign Application Priority Data

May 18, 2010    (JP) .................................. 2010-114546

(51) Int. Cl.
*A61B 1/005* (2006.01)
*A61B 1/00* (2006.01)
(Continued)

(52) U.S. Cl.
CPC .............. *A61B 1/0052* (2013.01); *A61B 1/005* (2013.01); *A61B 1/00078* (2013.01); *A61B 1/0016* (2013.01); *A61B 1/0057* (2013.01); *A61B 1/018* (2013.01); *A61B 1/313* (2013.01); *A61B 10/06* (2013.01); *A61B 17/29* (2013.01);
(Continued)

(58) Field of Classification Search
CPC ............. A61B 1/0052; A61B 1/00078; A61B 1/0016; A61B 1/0057

USPC ........... 606/1, 41–52; 600/139, 141, 142, 150
See application file for complete search history.

(56) References Cited

U.S. PATENT DOCUMENTS 6,030,382 A * 2/2000 Fleischman et al. ............ 606/41
2004/0193015 A1   9/2004 Ikeda et al.
(Continued)

FOREIGN PATENT DOCUMENTS

JP    Sho 62-154373    10/1987
JP    05-115432    5/1993
(Continued)

OTHER PUBLICATIONS

Japanese Official Action mailed Apr. 17, 2012 in corresponding Japanese Patent Application No. 2011-539208 together with partial English-language translation.
(Continued)

*Primary Examiner* — Aaron Roane
(74) *Attorney, Agent, or Firm* — Scully, Scott, Murphy & Presser, PC

(57) ABSTRACT

A medical apparatus includes a distal end portion provided at a distal end of an insertion portion that has functions of performing inspection, treatment or observation, a bending portion provided with first and second ends and configured so as to bend in two or more directions by connecting the first end to the distal end portion and connecting a plurality of bending pieces, a bending portion operation unit provided in an operation section connected to a proximal end of the insertion portion that causes the bending portion to perform bending operation and a neutral position restoring elastic member fixed to the first end side and the second end side that generates elasticity for causing the bending portion to restore to a neutral position.

8 Claims, 6 Drawing Sheets

(51) Int. Cl.
    *A61B 10/06*     (2006.01)
    *A61B 17/29*     (2006.01)
    *G02B 23/24*     (2006.01)
    *A61B 1/018*     (2006.01)
    *A61B 1/313*     (2006.01)
    *A61B 17/00*     (2006.01)

(52) U.S. Cl.
    CPC ............ *A61B2017/00314* (2013.01); *A61B 2017/00398* (2013.01); *A61B 2017/2905* (2013.01); *G02B 23/2476* (2013.01)

(56) References Cited

U.S. PATENT DOCUMENTS

2007/0112255 A1    5/2007    Ikeda et al.
2008/0027285 A1    1/2008    Yasunaga
2008/0194911 A1    8/2008    Lee

FOREIGN PATENT DOCUMENTS

| JP | 6-44502 | 6/1994 |
| JP | 2011-095754 | 4/2001 |
| JP | 2002-048983 | 2/2002 |
| JP | 2003-230536 | 8/2003 |
| JP | 2008-183420 | 8/2008 |
| JP | 2009-089820 | 4/2009 |

OTHER PUBLICATIONS

Extended Supplementary European Search Report dated Oct. 29, 2012 issued in corresponding Application No. / Patent No. 11783467. 1-1265 PCT/JP2011061094.

* cited by examiner

MEDICAL APPARATUS

CROSS REFERENCE TO RELATED APPLICATION

This application is a continuation application of PCT/JP2011/061094 filed on May 13, 2011 and claims benefit of Japanese Application No. 2010-114546 filed in Japan on May 18, 2010, the entire contents of which are incorporated herein by this reference.

BACKGROUND OF THE INVENTION

1. Field of the Invention

The present invention relates to a medical apparatus provided with a bending portion configured by connecting a plurality of bending pieces to an insertion portion.

2. Description of the Related Art

In recent years, various medical apparatuses have been used to diagnose, extract and treat a living body in a medical field. Examples of such a medical apparatus include an endoscope provided with an observation optical system at a distal end portion thereof and a medical manipulator provided with a hand arm, a knife arm or the like at a distal end portion thereof.

Endoscopes and medical manipulators can be divided into a type with an insertion portion configured to be rigid and a type with an insertion portion provided with a bending portion. The bending portion has, for example, a multi-joint structure with a plurality of substantially ring-shaped bending pieces pivotably connected via connecting pins. The bending portion is configured to bend in two directions, up and down or four directions, up and down, left and right.

Japanese Patent Application Laid-Open Publication No. 2009-89820 and Japanese Patent Application Laid-Open Publication No. 2002-48983 disclose a type with the bending portion made up of a coil spring.

The bending portion formed into a multi-joint structure is configured to be bent by pulling or loosening a bending wire. The distal end portion of the bending wire is fixed to a distal end bending piece making up the distal end of the bending portion. On the other hand, the proximal end portion of the bending wire is fixed to a bending portion operation unit provided in an operation section.

According to this configuration, when bending the bending portion, for example, in an upward direction, an operator turns a rotary operation knob making up the bending portion operation unit in a predetermined direction. An upward bending wire fixed to the distal end bending piece is pulled as the rotary operation knob is turned, while a downward bending wire is loosened and the bending portion is bent in an upward direction.

When restoring the bending portion bent in the upward direction as described above to an original state, that is, an unbent state (also described as "neutral position" or "rectilinear state"), the operator returns the rotary operation knob to the original position, that is, turns the rotary operation knob in a direction opposite to the aforementioned direction. The downward bending wire is then pulled, while the upward bending wire is loosened and the bending portion is restored to the neutral position.

When the bending portion is returned to the neutral position by operating the rotary operation knob, in the bending portion configured by connecting a plurality of bending pieces, responsivity thereof deteriorates as the bending state of the bending portion approaches the neutral position. That is, the bending operation of the bending portion becomes dull relative to the amount of turning of the rotary operation knob. As a result, even when the rotary operation knob was returned to the original position, it was difficult to restore the bending portion to the rectilinear state and restoring it to the neutral position was particularly difficult on the bending portion distal end side. The deterioration of responsivity may be attributable to the fact that the bending wire is given a looseness beforehand and that friction is produced between a bending piece and a connecting pin connecting neighboring bending pieces or the like.

However, what is most important to the operator is that the bending portion performs accurate bending operation through operation of the rotary operation knob and a desired observed image is thereby obtained. Therefore, when the bending operation knob was returned to the original position, the operator did not take notice of whether or not the bending portion was restored to the neutral position.

On the other hand, medical apparatuses developed in recent years such as motor-driven bending endoscopes or motor-driven medical manipulators include a motor-driven bending portion at an insertion portion. A medical apparatus having a motor-driven bending portion is required, when the bending portion operation unit is set to a 0 point (origin), to be set at a neutral position where the bending portion is not bent in any direction, that is, a state in which the front is being observed which is the axial direction of the insertion portion in the case of a front viewing endoscope.

Regarding techniques for returning the bending portion to the neutral position, for example, Japanese Utility Model Laid-Open No. 6-44502 discloses a bending mechanism including a bent portion reconstruction member made of a shape memory alloy arranged inside the bent portion. Furthermore, Japanese Patent Application Laid-Open Publication No. 2008-183420 discloses a flexible endoscope wire spring guide including a coil pipe having reconstructing elasticity provided in a bending portion and a bending wire inserted in the coil pipe.

SUMMARY OF THE INVENTION

A medical apparatus according to one aspect of the present invention includes a distal end portion provided at a distal end of an insertion portion that has functions of performing inspection, treatment or observation, a bending portion provided with first and second ends and configured so as to bend in two or more directions by connecting the first end to the distal end portion and connecting a plurality of bending pieces, a bending portion operation unit provided in an operation section connected to a proximal end of the insertion portion that causes the bending portion to perform bending operation and a neutral position restoring elastic member fixed to the first end side and the second end side that generates elasticity for causing the bending portion to return to a neutral position.

DETAILED DESCRIPTION OF THE PREFERRED EMBODIMENT

Hereinafter, an embodiment of the present invention will be described with reference to FIG. 1 to FIG. 7.

Examples of a medical apparatus provided with a bending portion configured by connecting a plurality of bending pieces in an insertion portion include an endoscope 1 shown in FIG. 1 to FIG. 3 and a medical manipulator (hereinafter abbreviated as "manipulator") 10 shown in FIG. 4 and FIG. 5.

Figure 1:
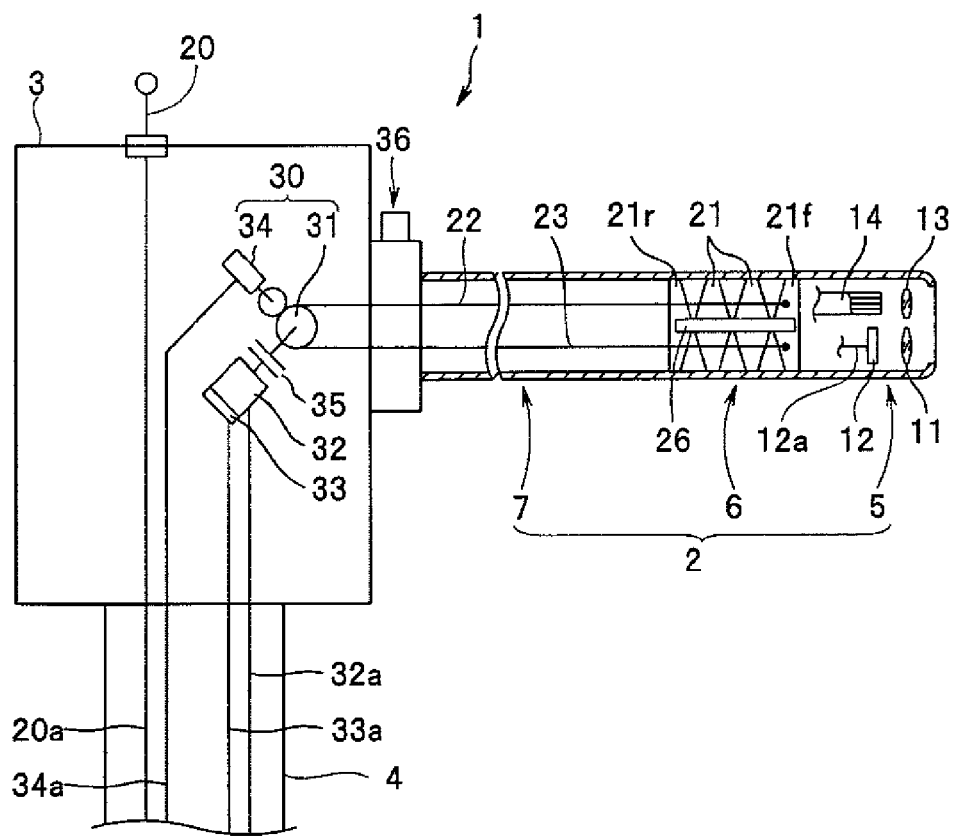
FIG. 1 is a diagram illustrating a configuration example of a motor-driven bending endoscope.

The endoscope 1 shown in FIG. 1 is, for example, a motor-driven bending endoscope and is provided with a motor-driven bending portion 6 on a distal end side of an insertion portion 2. The bending portion 6 is made to perform bending operation by a motor-driven bending drive section 30, which is a bending portion operation unit provided, for example, in an operation section 3.

The bending drive section 30 of the endoscope 1 is configured to be driven and controlled by a control section provided in a bending control apparatus (not shown), which is an outside apparatus connected to the endoscope 1.

The endoscope 1 is mainly configured by including the elongated insertion portion 2, the operation section 3 and a universal cord 4. The operation section 3 is connected to the proximal end side of the insertion portion 2 and the universal cord 4 extends from one side of the operation section 3.

The insertion portion 2 is configured by connecting a rigid, distal end rigid portion 5 provided at the distal end, the freely bendable bending portion 6 and a long and flexible, flexible tube portion 7. The bending portion 6 is provided on the proximal end side of the distal end rigid portion 5 and the flexible tube portion 7 is provided on the proximal end side of the bending portion 6.

The distal end rigid portion 5 is provided with an observation lens group 11 making up an observation optical system, an image pickup apparatus 12, and an illumination lens group 13 and a light guide 14 making up an illumination optical system or the like. The light guide 14 extends to an endoscope connector (not shown) passing through the insertion portion 2, the operation section 3 and the universal cord 4. The endoscope connector is connected to a light source device (not shown) which is an outside apparatus.

The illumination optical system is not limited to the light guide 14, but may also be configured to provide a light-emitting element such as an LED at the distal end rigid portion 5. In this configuration, an electric wire connected to the light-emitting element extends to the endoscope connector.

On the other hand, a signal cable 12a extends from the image pickup apparatus 12. The signal cable 12a extends to the electric connector provided, for example, in the endoscope connector passing through the insertion portion 2, the operation section 3 and the universal cord 4. The electric connector is connected to a video processor, which is an outside apparatus.

Figure 2:
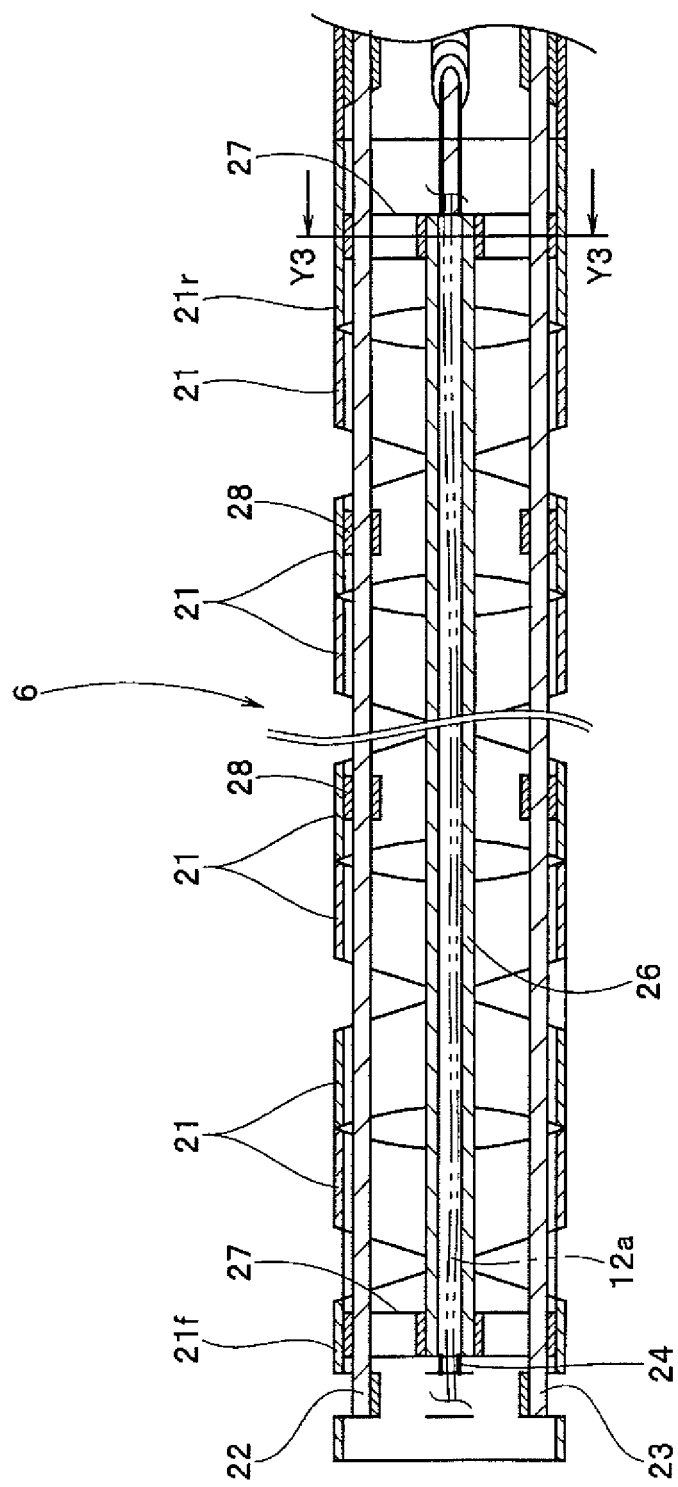
FIG. 2 is a diagram illustrating a configuration of a bending portion of the motor-driven bending endoscope provided with a neutral position restoring elastic member.

As shown in FIG. 1 and FIG. 2, the bending portion 6 is configured by connecting a plurality of bending pieces 21, so as to bend in four directions, up, down, left and right. A distal end bending piece 21f making up the distal end, which is a first end of the bending portion 6, is fixed to the distal end rigid portion 5. A proximal end bending piece 21r making up the proximal end, which is a second end of the bending portion 6, is fixed to the distal end side of the flexible tube portion 7.

Bending wires 22, 23, 24 and 25 are inserted in the insertion portion 2. The bending wire 22 is an upward bending wire for bending the bending portion 6 upward. The bending wire 23 is a downward bending wire for bending the bending portion 6 downward. The bending wire 24 is a rightward bending wire for bending the bending portion 6 rightward. The bending wire 25 (not shown) is a leftward bending wire for bending the bending portion 6 leftward.

The distal end portions of the bending wires 22, 23, 24 and 25 are respectively fixed at positions corresponding to up, down, left and right directions of the distal end bending piece 21f through, for example, brazing.

The bending portion 6 performs bending operation in a desired direction by pulling and loosening the bending wires 22, 23, 24 and 25 corresponding to the respective directions. The distal end rigid portion 5 is oriented toward a desired direction following the bending operation of the bending portion 6.

Lengths of the bending wires 22, 23, 24 and 25 are set to be longer by a predetermined length to have a predetermined looseness (or play) to prevent the bending wires 22, 23, 24 and 25 from being always tight.

A coil sheath 26 is disposed along the central axis of the bending portion 6. The coil sheath 26 is a neutral position restoring elastic member to restore the bending portion 6 to a neutral position and has predetermined elasticity. To be more specific, the coil sheath 26, in a predetermined arrangement condition in the bending portion 6, has elasticity to restore the bending portion 6 to the neutral position, which is a rectilinear state. In the present embodiment, the signal cable 12a, which is a built-in component in the insertion portion, is inserted in the coil sheath 26.

The coil sheath 26 is disposed along the central axis of the bending portion 6 by fixing the distal end portion thereof, which is a first end, to a fixing ring 27 fixed to the distal end bending piece 21f and fixing the proximal end portion thereof, which is a second end, to a fixing ring 27 fixed to the proximal end bending piece 21r.

Figure 3:
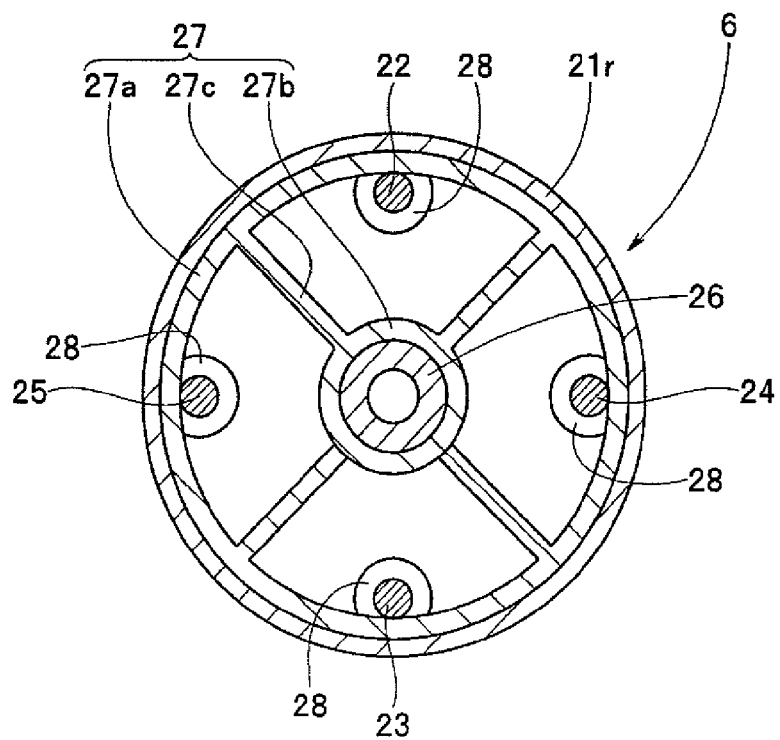
FIG. 3 is a cross-sectional view along a line Y3-Y3 indicated by arrows in FIG. 2.

As shown in FIG. 3, the fixing ring 27 is configured by including an outer circumferential ring 27a, an inner circumferential ring 27b and a support portion 27c. The outer circumferential ring 27a is a ring portion having a large diameter. One fixing ring 27 is integrally fixed to the distal end bending piece 21f by means of bonding, welding or the like with the outer circumferential face of the outer circumferential ring 27a disposed on the inner surface of the distal end bending piece 21f. On the other hand, the other fixing ring 27 is integrally fixed to the proximal end bending piece 21r by means of bonding, welding or the like with the outer circumferential face of the outer circumferential ring 27a disposed on the inner surface of the proximal end bending piece 21r.

The inner circumferential ring 27b is a ring portion having a smaller diameter than the outer circumferential ring 27a. The respective ends of the coil sheath 26 are arranged in inner holes of the inner circumferential ring 27b, which is a coil sheath fixing section, and integrally fixed to the respective fixing rings 27 by means of bonding, welding or the like.

The support portion 27c integrally holds and fixes the outer circumferential ring 27a and the inner circumferential ring 27b while keeping a predetermined distance therebetween.

In the present embodiment, the center of the inner hole of the inner circumferential ring 27b of the fixing ring 27 fixed to the distal end bending piece 21f and the center of the inner hole of the inner circumferential ring 27b of the fixing ring 27 fixed to the proximal end bending piece 21r are aligned with the central axis of the bending portion 6 as described above. The fixing ring 27 may have a structure in which the support portion 27c, the outer circumferential ring 27a and the inner circumferential ring 27b are integrated into one piece or a structure in which they remain as separate components.

In the case of the structure with separate components, one end of the support portion 27c is integrally fixed to the inner surface of the outer circumferential ring 27a by means of bonding, welding or the like. The other end of the support portion 27c is integrally fixed to the outer circumferential face of the inner circumferential ring 27b by means of bonding, welding or the like.

Furthermore, reference numeral 28 denotes a wire receiver. The wire receiver 28 is a bending wire insertion member and is integrally fixed to the inner surface of the fixing ring 27 and the inner surface of the bending piece 21 by means of bonding, welding or the like. The bending wires 22, 23, 24 and 25 are inserted in through holes of the respective wire receivers 28 corresponding to the bending direction.

As shown in FIG. 1, the operation section 3 is provided with the bending portion operation unit and the bending drive section 30. The bending portion operation unit is an apparatus that performs bending operation for causing the bending portion 6 to perform bending operation and is, for example, a joystick 20 disposed upright from the operation section 3 in the present embodiment.

In FIG. 1, of the bending wires 22 to 25, the upward and downward bending wires 22 and 23 are shown and the leftward and rightward bending wires 24 and 25 having a similar configuration are not shown and explanations thereof are omitted.

The bending drive section 30 is mainly configured by including a sprocket 31, a motor 32, an encoder 33 and a potentiometer 34. The proximal end portions of the bending wires 22 and 23 are fixed to the sprocket 31. The motor 32 drives the sprocket 31 to rotate clockwise or counterclockwise. The encoder 33 detects the rotation position of the motor 32. The potentiometer 34 detects the rotation position of the sprocket 31.

A signal line 32a extends from the motor 32. A signal line 33a extends from the encoder 33. A signal line 34a extends from the potentiometer 34. The signal lines 32a, 33a and 34a pass through the universal cord 4 and are electrically connected to predetermined locations of the control section of the bending control apparatus respectively.

Reference numeral 35 denotes a clutch. The clutch 35 is disposed between the sprocket 31 and the motor 32. The clutch 35 is operated manually or through operation of a clutch switch (not shown) to disconnect transmission of a drive force of the motor 32 to the sprocket 31 and enable the bending portion 6 to be set in a so-called "angle-free" state.

A signal line 20a that extends from the joystick 20 disposed upright from the operation section 3 of the present embodiment also passes through the universal cord 4 and is electrically connected to a predetermined location of the control section of the bending control apparatus.

The control section of the bending control apparatus generates a control signal for driving the motor 32 based on a bending operation instruction signal outputted when the joystick 20 is tilted, a detection signal outputted from the encoder 33 and a detection signal outputted from the potentiometer 34 and outputs the control signal to the motor 32. The motor 32 is driven based on the control signal and the sprocket 31 is rotated, and the bending wires 22 and 23 are thereby pulled or loosened. This causes the bending portion 6 to bend upward or downward according to the instruction from the joystick 20.

The operation section 3 is provided with a treatment instrument insertion port 36 from which a treatment instrument such as a manipulator 10 is inserted. The treatment instrument insertion port 36 communicates with a treatment instrument insertion channel (not shown) disposed inside the insertion portion 2. The treatment instrument inserted from the treatment instrument insertion port 36 passes through a channel opening (not shown) formed in the distal end rigid portion 5 via the treatment instrument insertion channel and is led out into the inside of the body.

Figure 4:
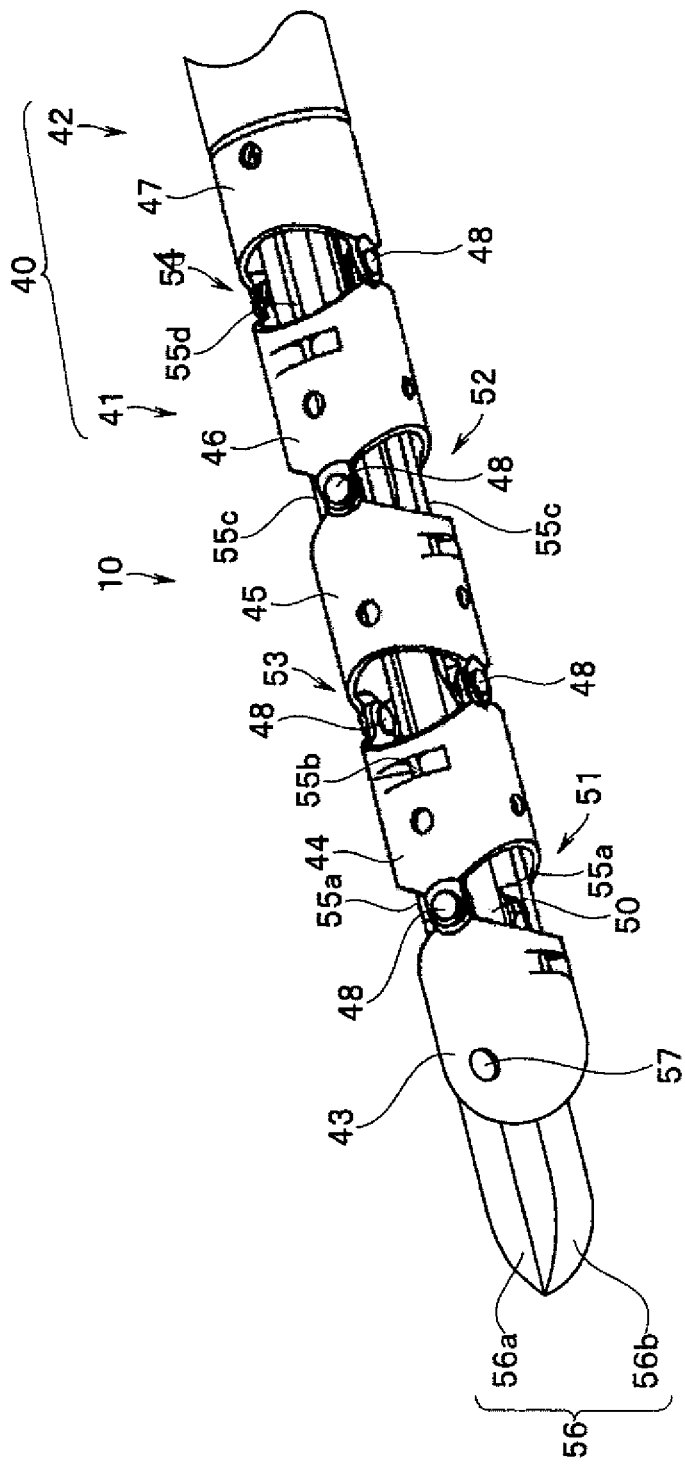
FIG. 4 is a perspective view illustrating a configuration example of a bending portion of a medical manipulator.
Figure 5:
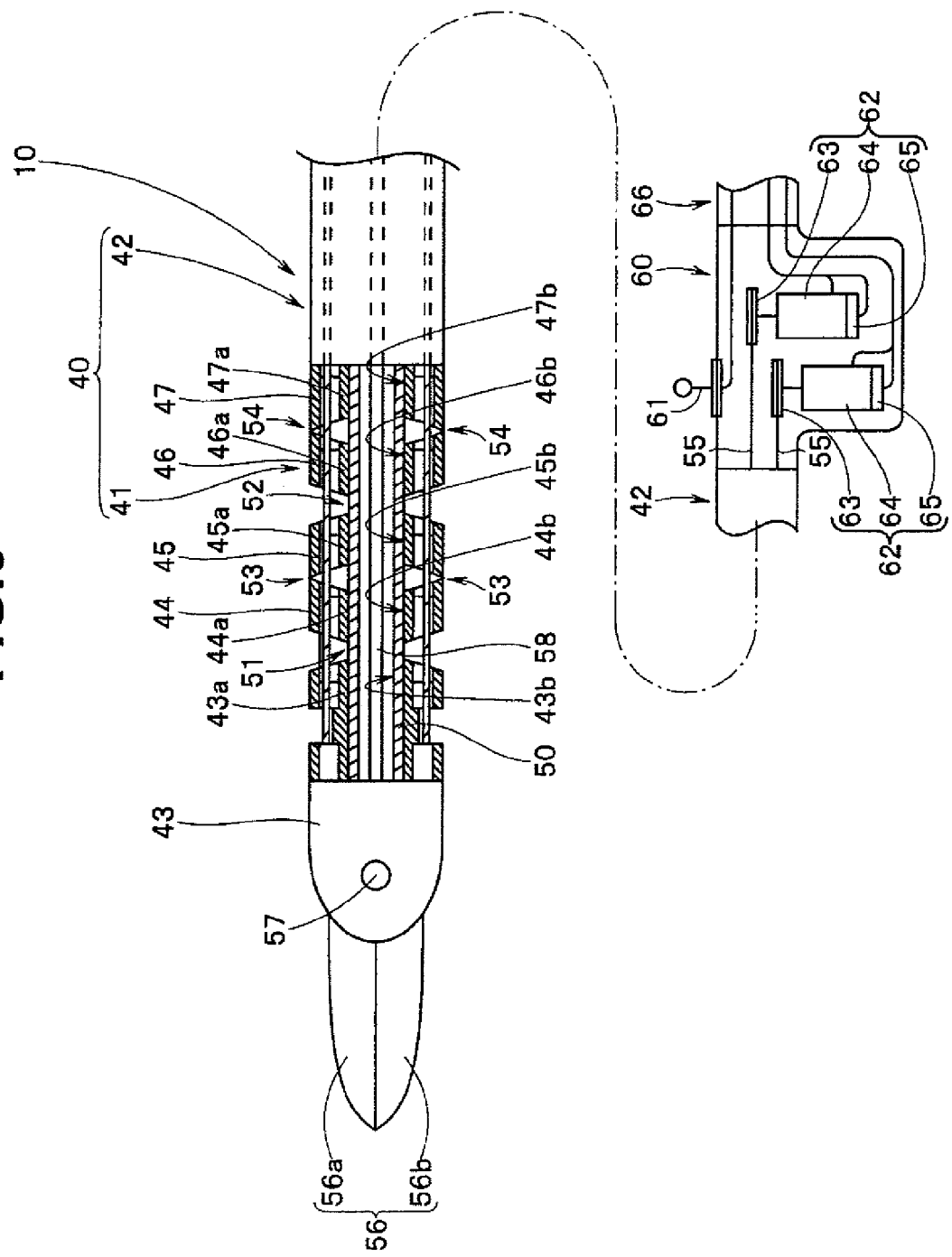
FIG. 5 is a diagram illustrating a configuration of the bending portion of the medical manipulator provided with the neutral position restoring elastic member.

The manipulator 10 shown in FIG. 4 and FIG. 5 is, for example, a biopsy forceps. The manipulator 10 is provided with a biopsy cup 56, which will be described later, at the distal end of an insertion portion 40.

The manipulator 10 is provided with a bending portion 41 at the insertion portion 40 and provided with a flexible tube portion 42 on the proximal end side. An operation section 60 from which, for example, a joystick 61 is disposed upright is provided on the proximal end side of the flexible tube portion 42. A plurality of bending drive sections 62 for causing the bending portion 41 to perform bending operation according to the angle of inclination of the joystick 61 is provided inside the operation section 60. The bending drive sections 62 of the manipulator 10 are driven and controlled by a control section provided in a bending control apparatus (not shown), which is an outside apparatus connected to the manipulator 10.

The bending drive section 62 is mainly configured by including a pulley 63, a motor 64 and an encoder 65. The proximal end of a bending wire 55 is fixed to the pulley 63. The motor 64 drives the pulley 63 to rotate clockwise or counterclockwise. The encoder 65 detects the rotation position of the motor 64. The rotation position of the pulley 63 is detected by, for example, a potentiometer (not shown). Reference numeral 66 denotes a control cable, which is connected to the bending control apparatus.

The bending portion 41 of the manipulator 10 is configured by connecting, for example, bending pieces 43 to 47. Coil sheath fixing sections 43a to 47a are integrally formed in the respective bending pieces 43 to 47 of the present embodiment. The coil sheath fixing sections 43a to 47a are provided with coil sheath fixing holes 43b to 47b. A coil sheath 50 is inserted into the coil sheath fixing holes 43b to 47b. The core centers of the coil sheath fixing holes 43b to 47b of the respective bending pieces 43 to 47 are formed so as to be aligned with the central axis of the bending portion 41.

The five bending pieces 43 to 47 are configured by pivotably connecting neighboring bending pieces via a connecting pin 48. The manipulator 10 of the present embodiment has two pitch drive joints 51 and 52 and two yaw drive joints 53 and 54.

The distal ends of pairs of bending wires 55a, 55b, 55c and 55d are integrally fixed to the bending pieces 43, 44, 45 and 46 making up the respective joints 51 to 54 at two locations on the diagonal by means of bonding, welding or the like. The bending wires 55a, 55b, 55c and 55d are pulled or loosened by the bending drive section 62 corresponding to each wire. In the manipulator 10, the biopsy cup 56 is configured to change the position and posture thereof by the bending pieces 43 to 46 bending around the respective joints 51 to 54.

The coil sheath 50 is a neutral position restoring elastic member and has predetermined elasticity. The coil sheath 50 is provided with elasticity to restore the bending portion 41 to the neutral position which is a rectilinear state. The coil sheath 50 is inserted into the coil sheath fixing holes 43b to 47b of the coil sheath fixing sections 43a to 47a formed in the respective bending pieces 43 to 47. The distal end portion, which is a first end of the coil sheath 50, is disposed in the coil sheath fixing hole 43b of the distal end bending piece 43 and integrally fixed by means of bonding, welding or the like. On the other hand, the proximal end portion, which is a second end of the coil sheath 50, is disposed in the coil sheath fixing hole 47b of the proximal end bending piece 47 and integrally fixed by means of bonding, welding or the like. Thus, the coil sheath 50 is disposed along the central axis of the bending portion 41.

The distal end bending piece 43 making up the farthest distal end of the bending portion 41, which also serves as the distal end portion of the insertion portion 40, is provided with the biopsy cup 56 which opens or closes. The biopsy cup 56 is configured by pivotably attaching a pair of cup members 56a and 56b to the distal end bending piece 43 via a pin 57. The cup members 56a and 56b are configured to open or close as a pulling wire 58, which is a built-in component in the insertion portion inserted in the coil sheath 50, moves forward or backward. The pulling wire 58 is configured to move forward or backward by a drive force of a drive section (not shown) provided in the operation section 60. The operator causes the pulling wire 58 to move forward or backward by a drive force of the drive section by operating, for example, a foot switch (not shown). The cup members 56a and 56b then perform opening/closing operation centered on the pin 57.

The manipulator 10 is not limited to the biopsy forceps but may also be an electric knife, marker or the like. In an electric knife, an electric wire that can pass a high-frequency current included in the insertion portion is inserted into the coil sheath 50. In the marker, a tube body that supplies a marker liquid, which is a built-in component in the insertion portion, is inserted into the coil sheath 50.

Operation of the endoscope system provided with the endoscope 1 and the manipulator 10 configured as described above will be described.

When inserting the insertion portion 2 into a target region of the inside of the body or observing a target region, the operator tilts the joystick 20. The motor 32 then starts to rotate, the bending wires 22 and 23 or the bending wires 24 and 25 are pulled or loosened as the motor 32 rotates and the bending portion 6 is bent in up and down, left and right directions. As a result, the operator can smoothly insert the insertion portion 2 into the body and observe the target region optimally.

Furthermore, the operator then causes the manipulator 10 to go out of the treatment instrument insertion port 36 of the operation section 3 into the body and then tilts the joystick 61. The bending portion 41 is then bent in a desired direction through the rotation of the motor 64 of the bending drive section 62. As a result, the operator can cause the biopsy cup 56 to confront with a polyp or the like discovered through endoscope observation.

Furthermore, the operator can drive the pulling wire 58 to move forward or backward by operating, for example, the foot switch, cause the biopsy cup 56 to open or close and extract a tissue peripheral to the polyp.

In the aforementioned endoscope 1, when the operator returns the joystick 20 to the upright position, the bending portion 6 gradually changes from a bent state to a rectilinear state as the motor 32 rotates. When elasticity of the coil sheath 26 provided along the central axis of the bending portion 6 surpasses the tension of the bending wires 22, 23, 24 and 25 inserted in the insertion portion 2, the bending portion 6 is restored to the neutral position by the elasticity of the coil sheath 26.

Meanwhile, in the aforementioned manipulator 10 as well, when the operator returns the joystick 61 to the upright position, the bending portion 41 gradually changes from a bent state to a rectilinear state as the motor 64 rotates. When the elasticity of the coil sheath 50 provided in the bending portion 41 surpasses the tension of the bending wires 55a, 55b, 55c and 55d inserted in the insertion portion 40, the bending portion 41 is restored to the neutral position by the elasticity of the coil sheath 50.

Thus, the coil sheath having predetermined elasticity is placed along the central axis of the bending portion of the medical apparatus and when the elasticity of the coil sheath surpasses the tension of the bending wire, the bending portion can be restored to the neutral position by the elasticity of this coil sheath.

Furthermore, the coil sheath is provided along the central axis of the bending portion and a signal cable, pulling wire, electric wire, tube body or the like which is a built-in component in the insertion portion is inserted in this coil sheath as appropriate. As a result, the built-in component in the insertion portion can always be disposed in the center of the bending portion regardless of the bending state of the bending portion.

This prevents excessive tension from being applied to the signal cable, pulling wire, electric wire, tube body or the like inserted in the coil sheath. This reliably prevents wire breakage in the signal cable or electric wire and reliably prevents the pulling wire and tube from being cut.

Furthermore, since the hole of the coil sheath is used as the insertion path of the built-in component in the insertion portion, it is possible to reduce the amount of filling in the bending portion.

The aforementioned embodiment adopts a configuration in which the fixing rings are provided in the distal end bending piece and the proximal end bending piece of the bending portion making up the insertion portion of the endoscope. However, the fixing rings may not only be placed at both ends of the distal end bending piece and the proximal end bending piece but also be fixed to a plurality of bending pieces arranged between the distal end bending piece and the proximal end bending piece respectively and the coil sheath may be inserted and arranged in the inner holes of the inner circumferential rings of the fixing rings.

This configuration allows an endoscope to be obtained which has operations and effects similar to those described above.

Furthermore, a configuration may also be adopted in which the coil sheath fixing section having the coil sheath fixing hole is provided for each of the plurality of bending pieces making up the bending portion of the endoscope, the coil sheath is placed in the coil sheath fixing hole and the respective ends of the coil sheath are fixed to the coil sheath fixing holes of the distal end bending piece and the proximal end bending piece.

This configuration allows an endoscope to be obtained which has operations and effects similar to those described above.

A configuration may also be adopted in which the fixing ring is provided in each of the distal end bending piece and the proximal end bending piece making up the bending portion of the manipulator, the respective ends of the coil sheath are arranged in the inner circumferential rings of the respective fixing rings and integrally fixed by means of bonding, welding or the like.

This configuration allows a medical manipulator to be obtained which has operations and effects similar to those described above.

Figure 6:
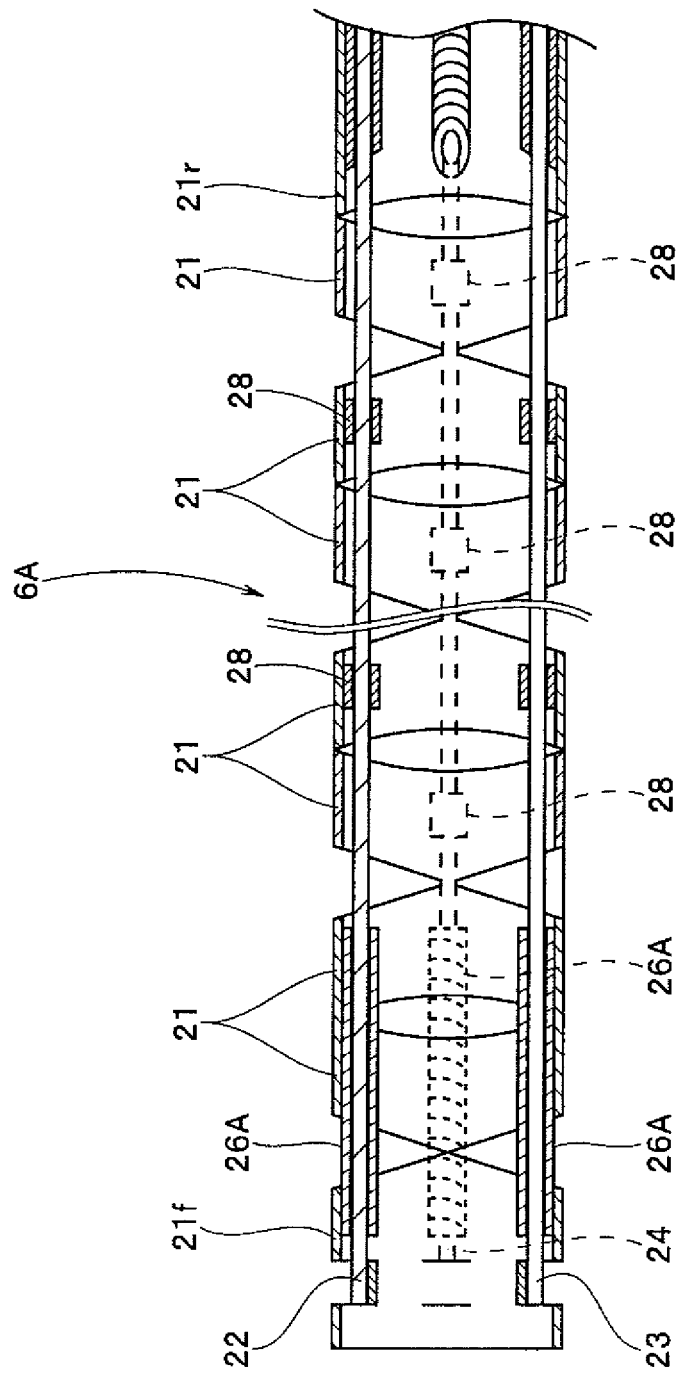
FIG. 6 is a diagram illustrating another configuration of the neutral position restoring elastic member provided in the bending portion.

Furthermore, as shown in FIG. 6, a plurality of coil sheaths 26A, which are neutral position restoring elastic members, may also be provided on the inner surface on the distal end side, which is a first end of a bending portion 6A.

The length of the coil sheaths 26A is set to a predetermined length. To be more specific, the distal end sides of the coil sheaths 26A are integrally fixed to the inner surface of the distal end bending piece 21*f* by means of bonding, welding or the like. On the other hand, the proximal end sides of the coil sheaths 26A are integrally fixed to the inner surface of a bending piece 21 located on the proximal end side separated from the distal end bending piece 21*f* by a predetermined number of bending pieces by means of bonding, welding or the like.

The coil sheath 26A set to a predetermined length is fixed at a position on the inner surface of the bending pieces 21*f* and 21 corresponding to the bending direction of the bending portion 6A so as to be parallel to the central axis of the bending portion 6A. The elasticity of the coil sheath 26A of the present embodiment is set to elasticity that restores the distal end side of the bending portion 6A to the neutral position.

In the present embodiment, in the case of the configuration in which the bending portion 6A is bent in two directions, up and down, the coil sheaths 26A are provided at respective positions corresponding to the upward direction and downward direction of the bending pieces 21*f* and 21. The bending wires 22 and 23 corresponding to the respective bending directions are inserted in the coil sheath 26A. That is, the coil sheath 26A also serves as the bending wire insertion member.

In the endoscope 1 provided with the aforementioned bending portion 6A, when the operator returns the joystick 20 to the upright position, the bending portion 6A gradually changes from a bent state to a rectilinear state as the motor 32 rotates. When the elasticity of the coil sheath 26A provided on the inner surfaces of the bending pieces 21*f*, 21 surpasses the tension of the bending wires 22, 23 inserted in the insertion portion 2, the distal end side of the bending portion 6A is restored to the neutral position by the elasticity of the coil sheath 26A and the entire bending portion 6A returns to the neutral position.

As described above, coil sheaths having a predetermined length and predetermined elasticity are provided on the inner surfaces on the distal end side of the plurality of bending pieces arranged on the distal end side of the plurality of bending pieces making up the bending portion in predetermined state. As a result, it is possible to restore the distal end side of the bending portion to the neutral position and restore the entire bending portion to the rectilinear state.

Furthermore, providing the coil sheaths only for the plurality of bending pieces on the distal end side of the bending portion can prevent increases in wire tension during bending operation compared to the configuration in which the coil sheath is provided over the total length of the bending portion. In addition, it is possible to prevent the amount of filling of the built-in component from increasing over the entire region of the bending portion.

In the case of a configuration in which the bending portion is bent in four directions, up and down, and left and right, the coil sheaths 26A are provided at positions corresponding to the directions, up and down, and left and right as shown by a broken line in FIG. 6. The bending wires 22 to 25 corresponding to the bending direction are inserted in each coil sheath 26A.

Furthermore, the neutral position restoring elastic member provided on the distal end side of the bending portion 6A is not limited to the coil sheath 26A, but may be, for example, a leaf spring. The leaf spring is provided with desired elasticity by setting appropriate sizes of width and thickness.

Figure 7:
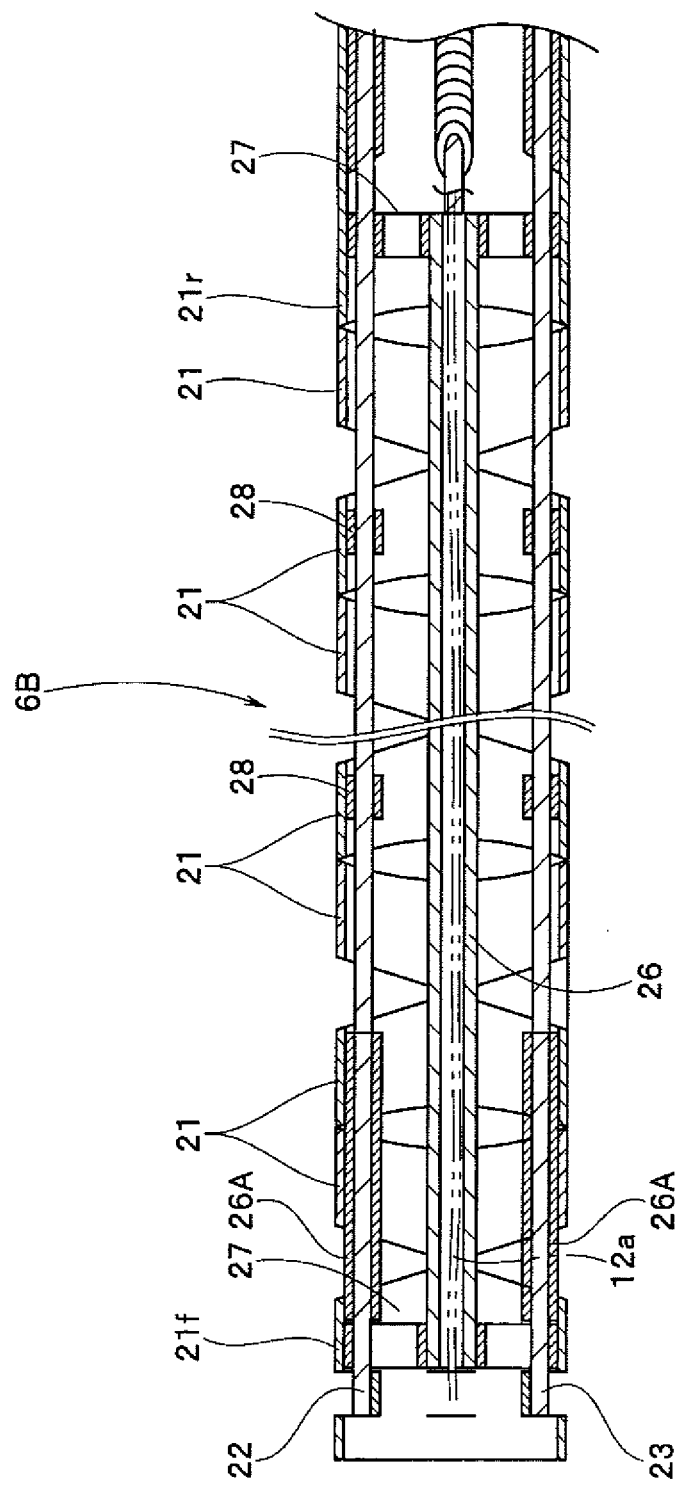
FIG. 7 is a diagram illustrating a further configuration of the neutral position restoring elastic member provided in the bending portion.

Furthermore, as shown in FIG. 7, the coil sheath 26 may be provided along the central axis of a bending portion 6B and the coil sheath 26A may be provided at predetermined positions on the inner surfaces of the distal end bending piece 21*f* making up the distal end side of the bending portion 6B and the bending piece 21 on the distal end side.

This configuration allows an endoscope to be obtained which has operations and effects similar to those described above.

The above-described embodiment in FIG. 6 and FIG. 7 has described the bending portion of the endoscope 1 as the bending portions 6A, 6B. However, the configuration of the bending portions 6A, 6B may also be provided in the bending portion 41 making up the manipulator 10. That is, the bending portion 41 may have a configuration with the coil sheath 26A provided on the distal end side of the bending portion 41 or a configuration with the coil sheath 26 provided along the central axis of the bending portion 41 and the coil sheath 26A also provided on the distal end side of the bending portion 41.

The above-described embodiment has described the motor-driven bending endoscope whose bending drive section is operated through operation of the bending portion operation unit. However, the bending portion operation unit is not limited to one motor driven to bend, but may also be, for example, an endoscope, or treatment instrument or the like whose operation section is provided with a bending operation knob which is manually operated to rotate.

The present invention is not limited only to the above-described embodiment, but may be implemented modified in various ways without departing from the spirit and scope of the invention.

What is claimed is:

1. A medical apparatus comprising:
   an insertion portion comprising:
      a distal end portion connected to a distal end of the insertion portion, the distal end portion having one or more that has functions of performing inspection, treatment or observation; and
      a bending portion provided with proximal and distal ends, the distal end of the bending portion being connected to a proximal end of the distal end portion, the bending portion being configured with a plurality of bending pieces so as to bend in two or more directions;
   a bending portion operation unit provided in an operation section connected to the proximal end of the insertion portion that causes the bending portion to bend in the two or more directions;
   a built-in component disposed in the insertion portion that extends from the distal end portion toward the operation section;
   a neutral position restoring elastic member that includes a first end and a second end and generates elasticity for causing the bending portion to return to a neutral position, the neutral position restoring elastic member being provided with an inner holes extending from the first end to the second end;
   a distal fixing ring including an outer circumferential ring fixed to an inner circumferential face of one of the plurality of bending pieces, an inner circumferential ring that fixes the first end of the neutral position restoring elastic member wherein the inner circumferential ring of the distal fixing ring is provided in the outer circumferential ring of the distal fixing ring; and a proximal fixing ring including an outer circumferential ring fixed to an inner circumferential face of an other of the plurality of bending pieces, and an inner circumferential ring that fixes the second end of the neutral position restoring elastic member, wherein the inner circumferential ring of the proximal fixing ring is provided in the outer circumferential ring of the proximal fixing ring;

wherein the built-in component disposed in the insertion portion is inserted in the inner hole.

2. The medical apparatus according to claim 1, wherein the neutral position restoring elastic member is one coil sheath provided along a central axis of the bending portion.

3. The medical apparatus according to claim 1, wherein the inner circumferential rings of the distal fixing ring and the proximal fixing ring are fixing holes which are provided to be aligned with a central axis of the bending portion and the neutral position restoring elastic member is placed in the fixing holes.

4. The medical apparatus according to claim 1, wherein the distal end portion is provided with a biopsy cup that opens or closes, and the built-in component in the insertion portion is a pulling wire that operates the biopsy cup.

5. The medical apparatus according to claim 4, wherein the biopsy cup includes a pair of cup members and a pin that pivotably attaches the pair of cup members to the bending pieces, and the pair of cup members are opened or closed by the pulling wire moving forward or backward.

6. The medical apparatus according to claim 1, wherein the distal end portion is provided with an image sensor, and the built-in component in the insertion portion is a signal cable that electrically connects the image sensor to the operation section.

7. The medical apparatus according to claim 1, wherein the outer circumferential ring of the distal fixing ring is fixed to a distal end bending piece.

8. The medical apparatus according to claim 1, wherein the outer circumferential ring of the proximal fixing ring is fixed to a proximal end bending piece.

* * * * *